United States Patent [19]

Doherty et al.

[11] Patent Number: 4,623,645

[45] Date of Patent: Nov. 18, 1986

[54] SUBSTITUTED CEPHALOSPORIN SULFOXIDES AS ANTI-INFLAMMATORY AND ANTIDEGENERATIVE AGENTS

[75] Inventors: James B. Doherty, New Milford; Bonnie M. Ashe, Scotch Plains; Paul E. Finke, Metuchen; Raymond A. Firestone, Fanwood; Shrenik K. Shah, Clark; Morris Zimmerman, Watchung, all of N.J.

[73] Assignee: Merck & Co., Inc., Rahway, N.J.

[21] Appl. No.: 485,979

[22] Filed: Apr. 18, 1983

[51] Int. Cl.$^4$ .................. C07D 501/20; A61K 31/545
[52] U.S. Cl. .................................... 514/200; 514/201; 514/204; 514/206; 540/215; 540/226; 540/227
[58] Field of Search ............ 544/21, 16, 26, 27; 424/246; 514/200, 201, 204, 206

[56] References Cited

U.S. PATENT DOCUMENTS

| | | |
|---|---|---|
| 3,936,446 | 2/1976 | Bentley et al. .................... 544/21 |
| 3,976,641 | 8/1976 | Hoover et al. .................... 544/21 |
| 4,272,439 | 6/1981 | Ganguly et al. .................. 544/21 |
| 4,296,111 | 10/1981 | Beattie et al. .................... 544/21 |
| 4,297,488 | 10/1981 | Christensen et al. ............ 424/246 |
| 4,381,300 | 4/1983 | Sheehan et al. .................. 544/21 |
| 4,446,318 | 5/1984 | Maito et al. ...................... 544/26 |
| 4,547,371 | 10/1985 | Doherty et al. .................. 544/16 |

*Primary Examiner*—Nicholas S. Rizzo

[57] ABSTRACT

Substituted cephalosporin sulfoxides are found to be potent elastase inhibitors and thereby useful anti-inflammatory/antidegenerative agents.

10 Claims, No Drawings

SUBSTITUTED CEPHALOSPORIN SULFOXIDES AS ANTI-INFLAMMATORY AND ANTIDEGENERATIVE AGENTS

BACKGROUND OF THE INVENTION

We have found that sulfoxides of substituted cephalosporins are potent elastase inhibitors and therefore are useful anti-inflammatory/antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 225, 9848 (1980); and B. Ashe et al., *J. Biol. Chem.*, 256, 11603 (1981);

(3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" Sci. Am. July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, TIBS, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction, H. Menninger et al., in *Biological Functions of Proteinases*, H. Holzer and H. Tschesche, eds. Springer-Verlag, Berlin, Heidelberg, New York, 1979, pp. 196–206.

Accordingly, an object of this invention is to discover new protease inhibitors, especially elastase inhibitors, useful for controlling tissue damage and various inflammatory or degenerative conditions mediated by proteases particularly elastase.

Another object of the present invention is to provide pharmaceutical compositions for administering the active substituted cephalosporin sulfoxides as protease inhibitors.

Still a further object to this invention is to provide a method of controlling inflammatory conditions by administering a sufficient amount of one or more of the active, substituted cephalosporin sulfoxides in a mammalian species in need of such treatment.

DETAILED DESCRIPTION OF THE INVENTION

This invention relates to cephalosporin sulfoxides as potent elastase inhibitors useful in the prevention, control and treatment of inflammatory conditions especially arthritis and emphysema.

Some of the cephalosporin free acids are known antibiotics which have been described in U.S. Pat. No. 4,297,488 issued Oct. 27, 1981.

The structural formula of the cephalosporin sulfoxide esters of the present invention are represented as follows:

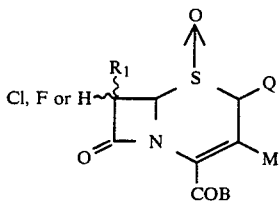
(I)

wherein M is:
(1) hydrogen;
(2) trifluoromethyl;
(3) chloro or fluoro;
(4) —COOH;
(5) —CHO; or
(6) —CH$_2$A wherein A represents
  (a) hydrogen;
  (b) halo;
  (c) hydroxy;
  (d) alkoxy;
  (e) aryloxy;
  (f) aralkyloxy;
  (g) unsubstituted or substituted mercapto;
  (h) acylthio;
  (i) acyloxy especially alkanoyloxy or arylcarbonyloxy such as acetoxy, benzyloxycarbonyloxy, benzoyloxy; and succinoyloxy; substituted or unsubstituted carbamoyl, thiocarbamoyl and N-alkyl or N,N-dialkyl derivatives thereof;
  (j) a quaternary ammonium group, for example, —⊕NH$_3$, —⊕NHE$^2$, or —⊕NE$^3$ where E represents loweralkyl, aryl or aralkyl;
  (k) unsubstituted or substituted amino or amido group especially —NH$_2$, —CONH$_2$ and N-alkyl or N,N-dialkyl derivatives thereof.

Thus, CH$_2$A can be a halomethyl such as chloromethyl, bromomethyl or fluoromethyl.

When CH$_2$A is a substituted hydroxy or substituted mercapto group, it can be shown by the formula

—CH$_2$ZR$_5$ where Z is oxygen or sulfur, and R$_5$ is an acyl group; a straight chain or branched chain loweralkyl, alkenyl or alkynyl group; an aryl group; an aralkyl group; or a heterocyclic group such as heteroaryl, heterocycloalkyl e.g., 1,3-dioxacyclohex-4-yl, piperidino, morpholino, oxacyclopropyl, pyrrolidino, tetrazolo, benzothiazolo, imidazolidino, pyrazolidino, and piperazino; or heterocycloalkenyl such as pyrrolino, 2-imidazolino, 3-pyrazolino or isoindolino. These groups can be unsubstituted or can be substituted by radicals such as alkyl, alkoxy, halo, cyano, carboxy, carbamoyl, azido,, sulfo, amino,, substituted amino, haloalkyl, carboxyalkyl, carbamoylalkyl, N-substituted carbamoylalkyl, guanidino, N-substituted guanidino, guanidoalkyl, sulfamyl, substituted sulfamyl, and the like. Representative of the —CH$_2$A groups are methoxymethyl, n-propoxymethyl, methylthiomethyl, acetoxymethyl, propionyloxymethyl, benzoyloxymethyl, (p-chlorobenzoyl)oxymethyl, succinoyloxymethyl, (p-methylbenzoyl)oxymethyl, pivaloyloxymethyl, D- or L-α-aminophenylacetyloxy, (1-adamantyl)-carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, [N-(carboxymethyl)-carbamoyl]oxymethyl, (N-p-sulfophenyl-carbamoyl)-oxymethyl, (N-p-carboxymethylphenyl-carbamoyl)-oxymethyl, methoxycarbonyloxymethyl, isobutanoyloxymethyl, cyclobutyl-carbonyloxymethyl, carbamoylthiomethyl, (ethoxythiocarbonyl)thiomethyl, (n-propoxythiocarbonyl)thiomethyl, (cyclopentanoxythiocarbonyl)thiomethyl, methylthiomethyl, N-N-diethylthiocarbamoylthiomethyl, N-methylpiperazinium-1-thiocarbonylthiomethyl, N,N-dimethylpiperazinium-1-thiocarbonylthiomethyl, 2-furoylthiomethyl, isothiouroniummethyl, (5-methyl-1,3,4-thiadiazol-2-yl)thiomethyl, p-tolylsulfonylthiomethyl, 2-benzothiazolothiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl.

Alternatively, when CH$_2$A is hydroxymethyl, the cephalosporin can also exist as the lactone which is formed by internal esterification with the adjacent carboxy group.

The substituent CH$_2$A can also be a group of the general formula

—CH$_2$Y$_1$ wherein Y$_1$ represents amino or substituted amino including nitrogen heterocycles and substituted heterocyclic groups as described in R$_5$. Y$_1$ may also be nitrogen which is part of the heterocyclic system as shown below.

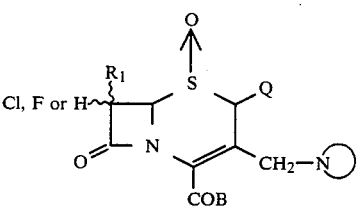

Examples of such groups that might be mentioned are aminomethyl, acetamidomethyl, carbamoylaminomethyl, N,N-dimethylaminomethyl, N-(2-chloroethyl)-aminomethyl, 5-cyano-triazol-1-yl-methyl, 4-methoxycarbonyltriazol-1-yl-methyl.

When A is amino the cephalosporin compound can also exist as the lactam formed by loss of water with the adjacent carboxy group.

Representative of the quaternary ammonium groups representing A that might be mentioned are pyridinium, 3-methylpyridinium, 4-methylpyridinium, 3-chloropyridinium, 3-bromopyridinium, 3-iodopyrinium, 4-carbamoylpyridinium, 4-(N-hydroxymethylcarbamoyl)pyridinium, 4-(N-carbomethoxycarbamoyl)-pyridinium, 4-(N-cyanocarbamoyl)pyridinium, 4-carboxymethylpyridinium, 4-hydroxymethylpyridinium, 4-trifluoromethyl-pyridinium, quinolinium, picolinium and lutidinium.

When A is mercapto, it may be —SH,

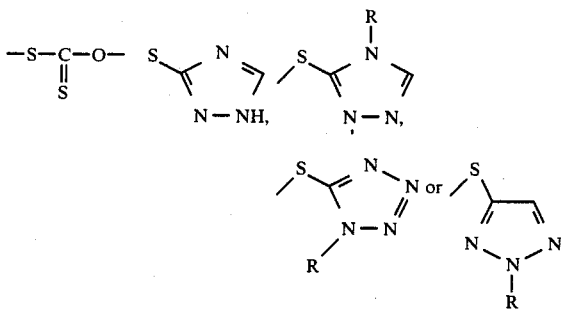

alkyl, alkylthio, arylthio, aralkylthio or heterocyclothio, wherein R represents $C_{1-6}$alkyl.

The preferred groups representing A are (a) hydrogen; (b) halo; (c) hydroxy; (d) alkoxy; (e) aryloxy; (f) aralkyloxy; (g) substituted or unsubstituted mercapto especially —SCOOR,

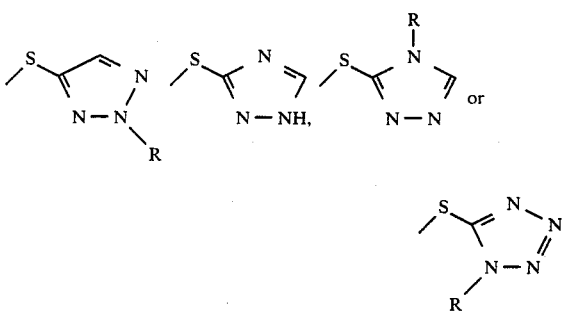

(h) acylthio; or (i) acyloxy. The acyl group can be a loweralkanoyl group of 2-6 carbon atoms such as acetyl, —COC$_2$H$_5$ or —COC$_3$H$_7$, carbamoyl, or thiocarbamoyl and N-alkyl or N,N-dialkyl derivatives thereof. The alkyl group of the foregoing substituents contains 1-10 carbon atoms and may be further substituted by radicals such as alkoxy, halo, amino, cyano, carboxy, sulfo, and the like. More preferably, A is
(a) alkanoyloxy especially

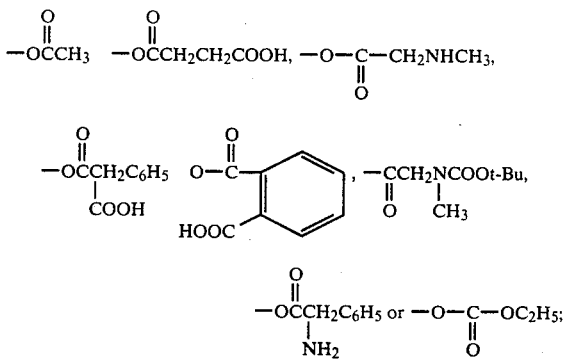

(b) $C_{1-3}$alkoxy especially methoxy, ethoxy or i- or n-propyloxy;
(c) halo;
(d) hydrogen;
(e) hydroxy;
(f) substituted or unsubstituted mercapto; or
(g) carbamoyloxy; especially L- or D- form of

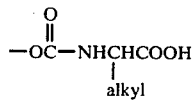

The substituent $R_1$ in formula (I) above can be
(a) nitrogen bonded group including R'NH— wherein R' is as defined below;
(b) hydrogen;
(c) hydroxy;
(d) mercapto;
(e) substituted oxy;
(f) substituted thio;
(g) hydrocarbyl or substituted hydrocarbyl group;
(h) cyano;
(i) carbonyl or thiocarbonyl containing substituents bonded by said carbonyl or thiocarbonyl radical;
(j) halo;
(k) phosphono or a substituted phosphono group.

When $R_1$ is R'NH—, R' represents a substituted or unsubstituted aliphatic, aromatic or heterocyclic, araliphatic or heterocyclylaliphatic carboxylic acid radical or a carbothioic acid radical such as the acyl radicals of the known cephalosporins and penicillins. These acyl radicals can be represented by the general formula

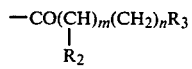

where $R_2$ is a radical of the group defined below, m and n represent 0–4 and $R_3$ represents R'' or ZR'', which are also defined below.

One group of the acyl radicals, i.e., when m and n are both 0 and $R_3$ is R'', can be represented by the general formula

wherein R'' is:
(a) straight or branched chain alkyl having from 1 to 20 carbon atoms especially methyl, trifluoromethyl, ethyl, isopropyl, t-butyl, pentyl or hexyl;
(b) aryl having from 6 to 10 carbon atoms especially phenyl, substituted phenyl or naphthalene;
(c) cycloalkyl having from 3 to 8 carbon atoms especially cyclopentyl, or cyclohexyl;
(d) alkenyl having from 2 to 20 carbon atoms especially $C_{2-6}$alkenyl such as vinyl, allyl, or butenyl;
(e) cycloalkenyl having from 5 to 8 carbon atoms especially cyclopentenyl or cyclohexenyl;
(f) alkynyl having from 2 to 20 carbon atoms especially $C_{2-6}$alkynyl for example, ethynyl, propynyl or hexynyl;
(g) alkoxy having from 1 to 10 carbon atoms especially $C_{1-3}$alkoxy such as methoxy, ethoxy or n-propoxy or i-propoxy;
(h) aralkyl, alkaryl, aralkenyl, aralkynyl, alkenylaryl or alkynylaryl wherein alkyl, aryl, alkenyl and alkynyl are as previously defined;

(i) monoheteroaryl, di- or polyheteroaryl, or fused heteroaryl containing from 1 to 3 of any one or more of the heteroatoms N, S or O in each heteroaryl ring thereof, for example, pyridyl, pyrryl, thienyl, isothiazolyl, imidazolyl, pyrazinyl, pyrimidyl quinolyl, isoquinolyl, benzothienyl, isobenzofuryl pyrazolyl, indolyl, purinyl, carbozolyl, isoxazolyl and the like;

(j) heteroarylalkyl such as 2-pyridylmethyl, 2-thienylmethyl and 3-isothiazolylethyl; or (k) hydrogen.

The above groups (a)–(b) can be unsubstituted or can be substituted by radicals such as alkyl, alkoxy, halo such as fluoro, chloro, bromo or iodo, cyano, carboxy, sulfoamino, carbamoyl, sulfonyl, azido, amino, substituted amino such as monoalkylamino and dialkylamino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R" is methoxy, ethoxy, benzyl, p-hydroxybenzyl, 3- or 4-nitrobenzyl, p-aminobenzyl, o-aminobenzyl, m-aminobenzyl, o-sulfobenzyl, p-carboxymethylbenzyl, p-carbamoylmethylbenzyl, m-fluorobenzyl, m-bromobenzyl, p-chlorobenzyl, p-methoxybenzyl, p-aminomethylbenzyl, hydrogen, methyl, ethyl, cyanomethyl, 2-pentenyl, n-amyl, n-heptyl, phenethyl, difluoromethyl, trifluoromethyl, dichloromethyl, dibromoethyl, 1-(3-methylimidazolyl)-methyl, 2- or 3-(5-carboxymethylthienyl)methyl, 2- or 3-(4-carbamoylthienyl)-methyl, 2- or 3-(5-methylthienyl)-methyl, 2- or 3-(5-methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)-methyl, 3-(4-methoxy-1,2,5-thiadiazolyl)methyl, 2-furylmethyl, 2-(5-nitrofuryl)methyl, 3-furylmethyl, 2-thienylmethyl, and tetrazolylmethyl. The term "sulfo" represents mercapto or thio, sulfinyl and sulfonyl.

The acyl group can also be a radical of the formula

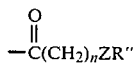

wherein n is 0–4, Z represents oxygen, sulfur or nitrogen, and R" is defined as above. Representative members of the substituent

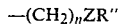

are allylthiomethyl, allylaminomethyl, phenylthiomethyl, butylmercaptomethyl, α-chlorocrotylmercaptomethyl, phenoxymethyl, phenylaminomethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)-phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-carboxymethyl)phenylthiomethyl, 2-pyrimidinylthiomethyl, phenethylthiomethyl, 1-(5,,6,7,8-tetrahydronaphthyl)-oxomethyl, 6,8-bis(methylthio)octanoyl.

Furthermore, the acyl group can be a radical of the formula

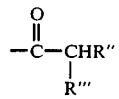

wherein R" is defined as above and R''' is a radical such as amino, hydroxy, azido, carbamoyl, guanidino, alkanoyloxy, halo, sulfamino, tetrazolyl, sulfo, carboxy, carbalkoxy, and the like. Representative members of the substituent

are α-aminobenzyl, α-amino-2-thienyl, α-methylaminobenzyl, α-amino-*-methylmercaptopropyl, α-amino-3 or 4-chlorobenzyl, α-amino-3 or 4-hydroxybenzyl, α-amino-2,4-dichlorobenzyl, α-amino-3,4-dichlorobenzyl, D(−)-α-hydroxybenzyl, α-carboxybenzyl, α-amino-3-thienyl, α-amino-2-thienyl, D(−)-α-amino-3-chloro-4-hydroxybenzyl, D(−)-α-amino-3-thienyl, 1-aminocyclohexyl, α-(5-tetrazolyl)benzyl, α-sulfaminobenzyl, α-sulfamino-3-thienyl, α-(N-methylsulfamino)benzyl, D(−)-α-guanidino-2-thienyl, D(−)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-oxadiazolyl)-carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienylhydroxymethyl, 2-(5-chlorothienyl)-carboxymethyl, 3-(1,2-thiazolyl)aminomethyl, 3-(1,2-thiazolyl)hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, 2-azidooctyl-3-phenyl-3-azidomethyl, α-sulfobenzyl, and α-phosphonobenzyl.

Alternatively, the group

can be an unsubstituted or substituted alkyl or aryl sulfonamido group such as phenylsulfonamido, ethylsulfonamido, trifluoromethane sulfonamido, benzylsulfonamido, 2,5-dimethylsulfonamido, 4-chlorophenylsulfonamido, 4-methoxyphenylsulfonamido, or an unsubstituted or substituted alkyl or aryl sulfonylalkylamino group such as $CH_3SO_2CH(CH_3)NH-$ or $C_6H_5SO_2CH_2NH-$, and the like.

Preferably, R' is:
(1) hydrogen;
(2)

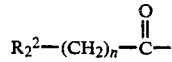

where $R^2$ represents:
(a) hydrogen;

(b) methyl or substituted methyl such as trifluoromethyl, cyanomethyl a methoxymethyl;
(c) thienyl;
(d) phenyl; or
(e) mono- and disubstituted phenyl and thienyl wherein the substituents are selected from the group consisting of chloro, bromo, fluoro, nitro, loweralkyl, and loweralkoxy;

n is 0 or 1; or (3)

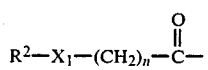

where $X_1$ is oxygen or sulfur; $R^2$ and n are as previously defined.

Even more preferably, R' is

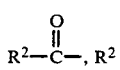

being selected from the group consisting of:
(1) trifluoromethyl;
(2) methyl;
(3) methoxy;
(4) hydrogen;
(5) benzyl;
(6) phenyl;
(7) 2-thienylmethyl;
(8) phenylthiomethyl;
(9) phenoxymethyl;
(10) benzyloxy, or
(11) $NCCH_2SCH_2$.

The oxy or thio substituent represented by $R_1$ in formula (I) can be a substituted hydroxy or mercapto group such as $-XR'_1$ wherein X is oxygen or sulfur and $R'_1$ is a hydrocarbyl group, preferably a straight or branched loweralkyl group of 1–6 carbon atoms, a straight or branched chain loweralkenyl or loweralkynyl group of 3–6 carbon atoms, a monocyclic aryl group such as phenyl, furyl, pyrryl and pyridyl, or an aralkyl group such as benzyl. These alkyl, alkenyl, alkynyl, aryl or aralkyl groups can be substituted with groups such as hydroxy, halo, nitro, amino, carboxy, thio, and the like. Other specific substituents represented by $R_1$ that might be mentioned are groups of the formula $-OAc$, $-SAc$, $-SO_3H$, $-SO_2NH_2$, $-OCD_3$, $-SO_2R_2$, $-SO_2NR_3R_4$, $-OCOOR_2$, $-SOR_2$, $-OCOSR_2$, $-OCONR_3R_4$, and the like wherein Ac represents an acyl group such as a formyl or loweralkanoyl, $R_3$ and $R_4$ represent hydrogen, loweralkyl, acyl and loweralkoxy, and $R_2$ represents loweralkyl, haloloweralkyl, aryl, aralkyl and substituted derivatives of such groups.

When $R_1$ is hydrocarbyl it can be straight or branched loweralkyl, straight or branched lower-alkenyl, loweralkynyl, aralkyl, cycloalkyl, a monocyclic aryl group, or a monocyclic heterocyclic group which can also be substituted with one or more groups such as halo, hydroxy, alkoxy, amino, nitro, sulfonyl, sulfamoyl, acyloxy, carbamoyloxy, carboxy, carboxamido and N-substituted carboxamido. Representative examples of such groups are $C_{1-6}$alkyl such as methyl, trifluoromethyl, ethyl, n-propyl, isopropyl, t-butyl; $C_{2-6}$alkenyl especially allyl, α-butenyl; $C_{2-6}$alkynyl such as ethynyl and methylethynyl; loweraralkyl such as benzyl, p-methoxybenzyl, phenethyl; phenyl, p-aminophenyl; cyclopropyl, cyclopentyl and 4-hydroxycyclohexyl;

$R_1$ in formula (I) above may also represent cyano or a group of the general formula

wherein X' is oxygen or sulfur, and R" is hydrogen, halo, hydroxy, mercapto, amino, substituted amino, alkyl, aryl, aralkyl, aralkoxy such as benzyloxy, alkoxy or aryloxy such as phenoxy, pyrroloxy, furyloxy, and thienyloxy, alkylthio or arylthio. Examples of these substituents are $-COOH$, $-CSSH$, $-COR_2$, $-COOR_2$, $-COSR_2$, $-CSSR_2$, $-CONH_2$, $-CSNH_2$, $-CSR_2$, $-CONHR_2$, $-CSNH$, $-CONR_3R_4$ and $-CSNR_3R_4$ wherein $R_2$ represents a straight or branched chain alkyl group of 1–6 carbon atoms and $R_3$ and $R_4$ represent hydrogen or $R_2$;

Furthermore, $R_1$ in formula (I) above represents a nitrogen bonded group such as amino, substituted amino groups, nitro, azido, nitroso, isocyanato, isothiocyanato and hydroxyamino. Specific examples of nitrogen bonded groups that might be mentioned are $-N_3$, $-NH_2$, $-NHR_2$, $NR_2R_3$, wherein $R_2$ represents a straight or branched chain loweralkyl group of 1 to 6 carbon atoms, $R_3$ represents $R_2$ or hydrogen, and n represents the integer 1 or 2.

Finally, the substituent $R_1$ in formula (I) represents phosphono or a metal or ammonium salt thereof, or a substituted phosphono group of the formula:

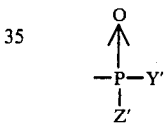

where Y' and Z' are the same or different and represent $-OR_2$, $-NR_3R_4$,

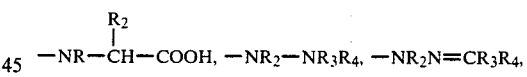

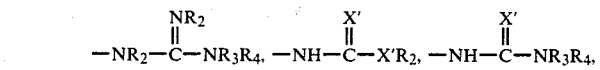

$-NC=X'$, $-OCOR_2$ and $-N_3$, where $R_2$ represents hydrogen or a hydrocarbyl radical, $R_3$ and $R_4$ represent hydrogen, hydrocarbyl, alkoxy or an acyl radical, and X' represents oxygen or sulfur.

Preferably, $R_1$ is
(1) R'NH— where R' represents acyl;
(2) hydroxy;
(3) $OR_1'$ where $R_1'$ represents hydrocarbyl group;
(4) $C_{1-6}$alkylthio;
(5) $C_{1-6}$alkylsulfinyl;
(6) $C_{1-6}$alkylsulfonyl;
(7) halo such as fluoro, chloro, bromo or iodo; or;
(8) hydrogen;
(9) $N_3$—; or
(10) $C_{1-6}$alkyl.

Even more preferably, $R_1$ is
(1) R'NH' where R' represents:
(a) $CH_3CO$—;
(b) $CF_3CO$—;

(c) HCO—;
(d) methoxycarbonyl;
(2) $C_{1-3}$alkyl;
(3) hydroxy;
(4) $OR_1'$ where $R_1'$ is
  (a) $C_{1-6}$alkyl especially methyl, ethyl, n-propyl;
  (b) —$C_6H_5$;
  (c) —$CH_2CH_2C_6H_5$; or
  (d)

where R represents hydrogen, $C_{1-6}$alkyl, phenyl, substituted or unsubstituted benzyl, or $C_{1-6}$alkylamino such as $CH_3NH—$, $C_2H_5NH—$;
(5) halo especially Cl or F; or
(6) —$SO_2R$.

B of Formula (I) above represents $OB_1$, or $NB_2B_3$ wherein $B_1$ and $B_2$ independently are:
  (a) straight or branched chain alkyl having from 1 to 20 carbon atoms, ethyl, isopropyl, t-butyl, pentyl or hexyl;
  (b) aryl having from 6 to 10 carbon atoms;
  (c) cycloalkyl having from 3 to 8 carbon atoms;
  (d) alkenyl having from 2 to 20 carbon atoms;
  (e) cycloalkenyl having from 5 to 8 carbon atoms;
  (f) alkynyl having from 2 to 20 carbon atoms;
  (g) alkoxy having from 1 to 10 carbon atoms;
  (h) aralkyl, alkaryl, aralkenyl, aralkynyl, alkenylaryl or alkynylaryl wherein alkyl, aryl, alkenyl and alkynyl are as previously defined;
  (i) loweralkenylalkyl;
  (j) alkanoylalkyl;
  (k) alkanoyloxyalkyl;
  (l) alkoxyalkyl;
  (m) alkanoyloxy;
  (n) a heterocyclic group including heterocyclic alkyl or heterocyclic alkenyl.

The above groups (a)–(n) can be unsubstituted or can be substituted by radicals such as alkyl, hydroxy, alkoxy, halo, nitro, mercapto, amino, substituted amino, cyano, carboxy, sulfoamino, carbamoyl, carbamoyloxy, sulfonyl, sulfinyl, sulfamoyl, azido, amino, substituted amino, carboxamido or N-substituted carboxamido; and $B_3$ is hydrogen or $B_1$. Representative examples of such groups are $C_{1-6}$alkyl especially methyl, ethyl or t-butyl, allyl, 3-butenyl, methoxyethyl, benzyl, p-carbomethoxybenzyl, m-carbomethoxybenzyl, p-sulfonylbenzyl, m-fluorobenzyl, o,p-dinitrobenzyl, o,p-dichlorobenzyl, p-methylbenzyl, m-methoxybenzyl, o-methylthiobenzyl, benzhydryl, $CH_2CH_2CH_2COOCH_3$, —$CH_2COOC_2H_5$, and the like.

Preferably $B_1$ and $B_2$ independently are substituted or unsubstituted
(1) aralkyl;
(2) aryl;
(3) straight or branched loweralkyl;
(4) straight or branched loweralkenyl;
(5) cycloalkyl;
(6) alkanoyloxyloweralkyl;
(7) alkanoylloweralkyl;
(8) alkoxyloweralkyl; or
(9) haloalkyl; and $B_3$ is H or $B_1$.

Even more preferably, $B_1$ and $B_2$ independently are substituted or unsubstituted
(1) benzyl;
(2) ethyl;
(3) t-butyl;
(4) —$CH_2CH_2CH=CH_2$ or $CH_2—CH=C(CH_3)_2$;
(5) —$CH_2CH_2CH_2COOt-Bu$;
(6) alkanoyloxymethyl; or
(7) alkanoylmethyl; and $B_3$ is H or $B_1$.

Q in formula (I) represents
(1) hydrogen;
(2) $C_{1-6}$alkyl especially methyl, ethyl, isopropyl, n-pentyl or n-hexyl;
(3) halo $C_{1-6}$alkyl especially chloro or fluoro $C_{1-6}$alkyl; or
(4) hydroxy $C_{1-6}$alkyl;
(5) methylene or substituted methylene especially $C_{1-6}$alkylmethylene, unsubstituted or substituted phenylmethylene, phenylthiomethylene, phenylsulfinylmethylene or phenylsulfonylmethylene;
(6) $C_{1-6}$alkoxy $C_{1-6}$alkyl;
(7) unsubstituted or substituted benzyl; or
(8) unsubstituted or substituted phenylthio $C_{1-6}$alkyl, phenylsulfonyl $C_{1-6}$alkyl;
(9) unsubstituted or substituted phenoxy $C_{1-6}$alkyl; or
(10) unsubstituted or substituted phenylamino $C_{1-6}$alkyl.

Preferably, Q is
(1) hydrogen;
(2) $C_{1-6}$alkyl;
(3) substituted or unsubstituted methylene;
(4) unsubstituted or substituted phenylthio $C_{1-6}$alkyl or phenylsulfonyl $C_{1-6}$alkyl.

Even more preferably, Q is
(1) hydrogen;
(2) methyl, ethyl or i- or p-propyl;
(3) methylene; or
(4) phenylthiomethyl or phenylsulfonylmethyl.

The cephalosporin sulfoxide esters of structural formula (I) where $OB_1$ is other than hydroxy can be prepared from the corresponding acid according to conventional methods of esterification.

For example,
(1) A compound of formula (I) is treated with a lower alkanol, a substituted or unsubstituted benzyl alcohol, or a substituted or unsubstituted benzhydrol(diphenylmethanol) in the presence of a catalyst such as sulfuric acid, hydrochloric acid and any one or a combination of the acid illustrated below in Table I.

TABLE I

Catalysts for Esterification (1) Hydrochloric acid or hydrobromic acid
(2) Sulfuric acid
(3) $C_{1-3}$alkanoic acid e.g. acetic acid
(4) Phosphoric acid
(5) Trifluoroacetic acid or anhydride
(6) Trichloroacetic acid
(7) p-Toluenesulfonic acid or other arylsulfonic acids
(8) Acidic ion-exchange resins with calcium sulfate
(9) Polymer-protected aluminum chloride, e.g., a complex between anhydrous aluminum chloride and polystyrene-divinyl benzene copolymer diphenylphosphitepyridine
(10) A Lewis acid such as boron trifluoride
(11) Aromatic sulfonylchloride-pyridine, e.g., p-toluenesulfonylchloride
(12) triphenylphosphine ditriflate

(13) dicyclohexylcarbodiimide (DCCD)
(14) β-trichloromethyl-β-pro-piolactone
(15) N,N'-carbonyldimidazole
(16) triphenylphosphinediethylazodicarbonylate
(17) 6-chlorobenzensulfonyloxybenzotriazole
(18) 1-methyl-2-halopyridinium iodide-tertiary amine (e.g., triethylamine).

at from about 0° to about 150° C. with or without refluxing until the esterification is substantially complete. Optionally, a solvent may be used to facilitate the reaction. The common solvents used are benzene, toluene, xylene, sulfolane-xylene, diethylether, tetrahydrofuran, 1,2-dimethoxyethane, dioxane and the like;

(2) A compound of formula (I) is converted to an acid halide such as acid chloride or bromide via treatment with a halogenating agent such as thionyl chloride, phosphorus penta- or oxychloride followed by reaction with an appropriate alcohol; and (3) Other methods such as alkylation of carboxylate salts (e.g., $K^+$, $Na^+$, $Ca^{++}$, $Ag^+$, $Cu^+$, tetralkylammonium-$R_4N^+$, any $Hg^{++}$ salts) of formula (I) with alkyl halides, for example, benzylchloride, benzyhydryl chloride; reaction with alkyl isoureas; treatment with diazomethane or diazophenylmethane ($C_6H_5CHN_2$); alcoholysis of anhydride derived from the cephalosporin acid corresponding to formula (I); transesterification with t-butyl esters or i-propenyl acetate and the like may also be used. These methods are disclosed in Saul Patai, editor, *The Chemistry of Functional Groups,* Supplement B, *The Chemistry of Acid Derivatives,* pp. 411–436, John Wiley & Sons, Chichester-New York-Brisbane-Toronto, 1979, and are incorporated herein by reference.

Other specific synthetic schemes which are useful in preparing the compounds of formula (I) are described in copending applications (Merck Cases 16855, 16865 and 16867), Ser. Nos. 485,978; 490,761; 490,617 filed 4-18-83; 5-2-83, 1983. These synthetic schemes are incorporated herein by reference.

This invention also relates to a method of treating inflammation in patients using a compound of Formula (I), particularly an especially preferred compound as the active constituent.

It has been found that the compounds of Formula (I) have anti-inflammatory/antidegeneration activity as shown below in Tables II to III by the effective inhibition of the proteolytic function of human granulocyte elastase.

TABLE II

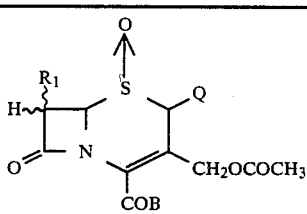

| $R_1$ | B | Q | $ED_{50}$ |
|---|---|---|---|
| —$OCH_3$ | $OCH_2\phi$ | H | 3.0 |
| —$OCH_3$ | $OCH_3$ | H | 8.0 |
| —F | OtBu | H | 2.0 |
| 7,7-dichloro | OtBu | H | 2.0 |

TABLE III

Protocol—Enzyme Assays for the Inhibition of Human Polymorphonuclear Leukocyte Elastase Via Hydrolysis of N-t-Boc-alanyl-alanyl-prolylalanine-p-nitroanilide Reagents:

0.05M TES (N-tris[hydroxymethyl]methyl-2-aminoethanesulfonic acid) buffer, pH 7.5.

0.2 mM N-t-Boc-alanyl-alanyl-prolyl-alanine-p-nitroanilide (Boc-AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (cephalosporin sulfoxide esters) to be tested dissolved in DMSO just before use.

ASSAY PROCEDURE

To 1.0 ml of 0.2 mM Boc-AAPAN in a cuvette, 0.01–0.1 ml of DMSO with or without inhibitor was added. After mixing, a measurement was taken at 410 mμ to detect any spontaneous hydrolysis due to presence of test compound. 0.05 Milliliters of PMN extract was then added and the ΔOD/min at 410 mμ was measured and recorded. Beckman model 35 spectrophotometer was used.

RESULTS

Results were reported as $ED_{50}$, i.e., effective dosage in micrograms per milliliter (μg/ml) for 50% inhibition of the enzyme activity 2 minutes after zero time.

COMMENTS

The elastase activity in the crude PMN extract may vary from one preparation to another. A control of each new batch is run, and the volume added in the assay procedure is adjusted according to activity.

Accordingly, the compounds of Formula (I) can be used to reduce inflammation and relieve pain in diseases such as emphysema, rheumatoid arthritis, osteoarthritis, gout, bronchial inflammation, infectious arthritis, rheumatic fever and the like.

For treatment of inflammation, fever or pain, the compounds of Formula (I) may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLE 1 t-Butyl 3-acetyloxymethyl-7α-methoxy-8-oxo-5-thia-1-azabicyclo(4.2.0)oct-2-ene-2-carboxylate-5-oxide Step A: Preparation of t-Butyl 3-acetyloxymethyl-7-diazo-8-oxo-5-thia-1-azabicyclo[4.2.0]oct-2-ene-2-carboxylate Into a two-liter Erlenmeyer flask is placed a solution of 7-ACA tert-butyl ester (7-ACA=3-acetyloxymethyl-7β-amino-8-oxo-5-thia-1-azabicyclo[4.2.0]oct-2-ene-2-carboxylate (22.22 g; 0.067 mol) in $CH_2Cl_2$ (500 ml). To this solution was added a mixture of sodium nitrite (4.68 g, 0.067 mol) in water (500 ml). The resulting two-phase mixture was cooled in an ice bath, and then 2N aqueous $H_2SO_4$ (51 ml) was added dropwise over 30 minutes with vigorous stirring. Stirring was continued for one hour at 0°, then the layers were separated and the aqueous layer was washed with methylene chloride (200 ml). The organic layers were combined, washed with brine (250 ml), dried over $MgSO_4$, and filtered to give a yellow solution of the diazo product which is used directly in the next reaction.

Step B: Preparation of t-Butyl 3-acetyloxymethyl-7α-methoxy-8-oxo-5-thia-1-azabicyclo[4.2.0]oct-2-ene-2-carboxylate The solution of t-butyl 3-acetyloxymethyl-7-diazo-8-oxo-5-thia-1-azabicyclo[4.2.0]oct-2-ene-2-carboxylate was cooled in an ice bath, and methanol (525 ml) was added. To this chilled mixture was added Rhodium (II) acetate dimer (210 mg), and the reaction mixture was stirred for 45 minutes, during which time the color changes from yellow to green-brown. The reaction mixture was filtered through silica gel, concentrated and dried in vacuo to give a dark red oil which was then purified by preparative high-pressure liquid chromatography to give 9.62 g (41.4%) of t-butyl 3-acetyloxymethyl-7α-methoxy-8-oxo-5-thia-1-azabicyclo[4.2.0]oct-2-ene-2-carboxylate as a yellow oil.

Step C: Preparation of t-Butyl 3-acetyloxymethyl-7α-methoxy-8-oxo-5-thia-1-azabicyclo[4.2.0]-oct-2-ene-2-carboxylate-5-oxide A solution of 1.002 g (2.92 mmol) of t-butyl 3-acetyloxymethyl-7α-methoxy-8-oxo-5-thia-1-azabicyclo-[4.2.0]oct-2-ene-2-carboxylate in 10 ml of $CH_2Cl_2$ was cooled to −78°. A solution of 0.505 g (80–90% pure) of m-chloroperbenzoic acid in 10 ml $CH_2Cl_2$ was dropped into the cold solution over 5 minutes. After 1 hour, the cold reaction mixture was poured into 7% sodium bicarbonate solution containing excess sodium sulfite and extracted with $CH_2Cl_2$. The combined $CH_2Cl_2$ layer was washed with brine and dried over $Na_2SO_4$. The concentrated filtrate was flash chromatographed with 20% acetone-$CH_2Cl_2$ to obtain 0.837 g (80% yield) of t-butyl 3-acetyloxymethyl-7α-methoxy-8-oxo-5-thia-1-azabicyclo[4.2.0]oct-2-ene-2-carboxylate-5-oxide as a mixture of sulfoxide isomers. Careful chromatography of this mixture furnished pure t-butyl 3-acetyloxymethyl-7α-methoxy-8-oxo-5-thia-1-azabicyclo[4.2.0]oct-2-ene-2-carboxylate-5β-oxide, m.p. 87°; $^1H$ NMR ($CDCl_3$); δ1.57 (s, 9), 2.12 (s, 3), 3.5 (d, 1, 18 Hz), 3.63 (s, 3), 4.06 (d, 1, 18 Hz), 4.45 (d, 1 2 Hz), 4.7 (d, 1, 13 Hz), 4.95 (bs, 1), 5.07 (d, 1, 13 Hz) and pure t-butyl 3-acetyloxymethyl-7α-methoxy-8-oxo-5-thia-1-azabicyclo[4.2.0]-oct-2-ene-2-carboxylate-5α-oxide, $^1H$ NMR ($CDCl_3$); δ1.58 (s, 9), 2.1 (s, 3), 3.25 (dd, 1, 18 Hz, 2 Hz), 3.62 (s, 3), 3.78 (d, 1, 18 Hz), 4.37 (t, 1, 2 Hz), 4.62 (d, 1, 14 Hz), 5.02 (d, 1, 2 Hz), 5.18 (d, 1, 14 Hz).

EXAMPLE 2 t-Butyl 3-acetyloxymethyl-7α-fluoro-8-oxo-5-thia-1-azabicyclo[4.2.0]oct-2-ene-2-carboxylate-5-oxide Step A: Preparation of t-Butyl 3-acetyloxymethyl-7α-fluoro-8-oxo-5-thia-1-azabicyclo[4.2.0]oct-2-ene-2-carboxylate t-Butyl 3-acetyloxymethyl-7-diazo-8-oxo-5-thia-1-azabicyclo[4.2.0]oct-2-ene-2-carboxylate was prepared from 10 mmoles 7-amino derivative in the same manner as described in Step A, Example 1, and taken up in 25 ml dry methylene chloride. To it with stirring was added dropwise over 30 seconds 0.60 ml 70% HF in pyridine. The mixture was stirred 2.5 minutes more and then washed with aq $K_2HPO_4$, water, aq $H_3PO_4$ and brine. It was dried with $MgSO_4$, filtered and chromatographed on 16 g silica gel with 1:1 hexane-ethyl acetate, affording 183 mg t-butyl 3-acetyloxymethyl-7α-fluoro-8-oxo-5-thia-1-azabicyclo[4.2.0]oct-2-ene-2-carboxylate. IR(μ): 5.57, 5.76. NMR (δ, $CDCl_3$): 1.54 s, t-Bu; 2.08 s, Ac; 3.34 d of d, J=18, 1.9 Hz, and 3.58 d of d, J=18, 0.8 Hz, $SCH_2$; 4.75 d, J=13 Hz and 4.97 d, J=13 Hz, $CH_2OAc$; 4.90 d of d, J=9, 1.6 Hz, CHS; 5.32 d of d, J=54, 1.6 Hz, CHF. MS: 332.

Step B: Preparation of t-Butyl 3-acetyloxymethyl-7α-fluoro-8-oxo-5-thia-1-azabicyclo[4.2.0]oct-2-ene-2-carboxylate-5-oxide Following substantially the same procedure as described in Example 1, Step C, t-Butyl 3-acetyloxymethyl-7α-fluoro-8-oxo-5-thia-1-azabicyclo[4.2.0]-oct-2-ene-2-carboxylate in 20 ml methylene chloride was oxidized to t-butyl 3-acetyloxymethyl-7α-fluoro-8-oxo-5-thia-1-azabicyclo[4.2.0]oct-2-ene-2-carboxylate-5-oxide.

EXAMPLE 3 t-Butyl 3-acetyloxymethyl-7α-chloro-8-oxo-5-thia-1-azabicyclo[4.2.0]oct-2-ene-2-carboxylate-5-oxide Step A: Preparation of t-Butyl 3-acetyloxymethyl-7α-chloro-5-thia-1-azabicyclo[4.2.0]oct-2-ene-2-carboxylate Following the same procedure as described in Step A, Example 1, 7-AcA t-butyl ester was diazatized to t-Butyl 3-acetyloxymethyl-7-diazo-8-oxo-5-thia-1-azabicyclo[4.2.0]oct-2-ene-2-carboxylate which was taken up into 2 ml EtOH, and treated with 0.1 ml aq. (~6N) HCl. There was an instantaneous vigorous effervescence. After 15 seconds, aq $K_2HPO_4$ and methylene chloride were added. The methylene chloride layer was separated, washed with aq $H_3PO_4$ and brine, dried with $MgSO_4$, filtered and chromatographed by PLC on silica gel, eluting with 25:1 $CHCl_3$-EtOAc, to provide 61 mg pure t-Butyl 3-acetyloxymethyl-7α-chloro-5-thia-1-azabicyclo[4.2.0]oct-2-ene-2-carboxylate. NMR($CDCl_3$): δ1.55 s, t-bu; 2.10 s, Ac; 3.40 d, 3.59 d, J=18 Hz, $SCH_2$; 4.79 d, 5.03 d, J=13 Hz, $CH_2OAc$; 4.70 d, J=1.5 Hz, CHS; 4.78 d, J=1.5 Hz, CHCl.

Step B: Preparation of t-Butyl 3-acetyloxymethyl-7α-chloro-8-oxo-5-thia-1-azabicyclo[4.2.0]oct-2-ene-2-carboxylate-5-oxide t-Butyl 3-acetyloxymethyl-7α-chloro-5-thia-1-azabicyclo[4.2.0]oct-2-ene-2-carboxylate was oxidized with MCPBA in methylene chloride as described in Example 1, Step C, to t-butyl 3-acetyloxymethyl-7α-chloro-8-oxo-5-thia-1-azabicyclo[4.2.0]oct-2-ene-2-carboxylate-5-oxide.

EXAMPLE 4 t-Butyl 3-hydroxycarboxylethylcarbonyloxymethyl-7α-methoxy-8-oxo-5-thia-1-azabicyclo[4.2.0]oct-2-ene-2-carboxylate-5-oxide Step A: Preparation of t-Butyl 3-hydroxycarbonyl-(n-propanoyl)oxymethyl-7α-methoxy-8-oxo-5-thia-1-azabicyclo[4.2.0]oct-3-ene-2-carboxylate A mixture of t-Butyl 3-hydroxymethyl-7α-methoxy-8-oxo-5-thia-1-azabicyclo[4.2.0]oct-3-ene-2-carboxylate (602 mg, 2.0 mmol) and succinic anhydride (300 mg, 3.0 mmol) were dissolved in dry tetrahydrofuran (4 ml) under nitrogen at room temperature, then 4-[N,N-dimethylamino]pyridine (300 mg, 2.5 mmol) was added with stirring. A solid began to separate out shortly after mixing. The mixture was allowed to stir 15 hours, then 50% saturated aqueous sodium bicarbonate (10 ml) was added, and the mixture was extracted with ether (2×20 ml). The combined ether extracts were washed with 50% sat. aq NaHCO₃ (10 ml), then the aqueous extracts were combined and acidified to pH 2.5 (using 1.0 M.H₃PO₄), the resulting cloudy solution was extracted with ethyl acetate (2×30 ml), then the organic layers were combined and washed with saturated brine (25 ml) and dried over Na₂SO₄. The solvent was removed in vacuo to give t-butyl 3-hydroxycarbonyl-(n-propanoyl)oxymethyl-7α-methoxy-8-oxo-5-thia-1-azabicyclo[4.2.0] oct-3-ene-2-carboxylate a yellow oil. This material was sufficiently pure to be carried on to the next step.

Step B: Preparation of t-Butyl 3-hydroxycarboxyl(n-propanoyl)oxymethyl-7α-methoxy-8-oxo-5-thia-1-azabicyclo[4.2.0]oct-2-ene-2-carboxylate-5-oxide The crude product t-Butyl 3-hydroxycarbonyl(n-propanoyl)oxymethyl-7α-methoxy-8-oxo-5-thia-1-azabicyclo[4.2.0]oct-3-ene-2-carboxylate from the above reaction is dissolved in methylene chloride and treated with m-chloroperbenzoic acid to give t-Butyl 3-hydroxycarboxyl(n-propanoyl)oxymethyl-7α-methoxy-8-oxo-5-thia-1-azabicyclo[4.2.0]oct-2-ene-2-carboxylate-5-oxide.

EXAMPLE 5 t-Butyl 3-chloromethyl-7α-methoxy-8-oxo-5-thia-1-azabicyclo[4.2.0]oct-2-ene-2-carboxylate-5-oxide To a solution of 0.9 g (3 mmol) of t-Butyl 3-hydroxymethyl-7α-methoxy-8-oxo-5-thia-1-azabicyclo[4.2.0]oct-3-ene-2-carboxylate in 20 ml of tetrahydrofuran was added 1 ml of pyridine. Thionyl chloride (0.5 ml) was added dropwise over 5 min. After stirring the reaction mixture for 0.5 hours, it was poured into ice-cold water and extracted with ethyl acetate. The combined extract was washed with 7.1 sodium bicarbonate solution, brine and dried over sodium sulfate. The concentrated filtrate was flash chromatographed wing 10% ethyl acetatehexane to yield 0.626 g (65%) yield of t-butyl 3-chloromethyl-7α-methoxy-8-oxo-5-thia-1-azacyclo[4.2.0]oct-3-ene-2-carboxylate as a pale yellow solid. m.p. 85°.

Following substantially the same procedures as described in Example 1, Step C, t-butyl 3-chloromethyl-7α-methoxy-8-oxo-5-thia-1-azabicyclo[4.2.0]oct-2-ene-2-carboxylate is oxidized to afford t-Butyl 3-chloromethyl-7α-methoxy-8-oxo-5-thia-1-azabicyclo[4.2.0]oct-2-ene-2-carboxylate-5-oxide.

EXAMPLE 6 m-Methoxycarbonylbenzyl-3-acetyloxymethyl-7α-methoxy-8-oxo-5-thia-1-azabicyclo[4.2.0]oct-2-ene-2-carboxylate-5-oxide Step A: Preparation of N,N'-diisopropyl-O-(m-methoxycarbonylbenzyl)isourea A mixture of 4.75 g (28.6 mmols) of m-methoxycarbonylbenzyl alcohol and 3.6 g (28.6 mmols) of N,N'-diisopropylcarbodiimide was stirred with 50 mg (0.51 mmols) of cuprous chloride at room temperature for 24 hours. The reaction was then diluted with 10 ml of hexane and eluted through a short column of neutral alumina with 20% ethyl acetate-hexane to give 8.0 g (96%) of N,N'-diisopropyl-O-(m-methoxycarbonylbenzyl)-isourea as a colorless oil.

Step B: Preparation of m-methoxycarbonylbenzyl 3-acetyloxymethyl-7α-methoxy-8-oxo-5-thia-1-azabicyclo[4.2.0]oct-2-ene-2-carboxylate A solution of 1.0 g (3.4 mmole) of N,N'-diisopropyl-O-(m-methoxycarbonylbenzyl)-isourea and 1.0 g (3.4 mmole) of 3-acetyloxymethyl-7α-methoxy-8-oxo-5-thia-1-azabicyclo[4.2.0]oct-2-ene-2-carboxylic acid in 2.0 ml of tetrahydrofuran (THF) was stirred for 24 hours at room temperature. The reaction was then cooled to −10° C., filtered and concentrated in vacuo. The product was purified by flash chromatography using a solvent gradient of 35 to 40% ethyl acetate-hexane to give 300 mg (20%) of m-methoxycarbonylbenzyl 3-acetyloxymethyl-7α-methoxy-8-oxo-5-thia-1-azabicyclo[4.2.0]oct-2-ene-2-carboxylate as an oil, NMR (CDCl₃) δ 2.04 (s, 3), 3.40 (ABq, 2, 18 Hz) 3.50 (s, 3), 3.87 (s, 3), 4.47 (d, 1, 2 Hz), 4.63 (d, 2, 2 Hz), 4.78 (ABq, 2, 13 Hz), 5.27 (ABq, 2, 13 Hz), 7.2–7.6 (m, 2), 7.7–8.0 (m, 2).

Step C: Preparation of m-methoxycarbonylbenzyl 3-acetyloxymethyl-7α-methoxy-8-oxo-5-thia-1-azabicyclo[4.2.0]oct-2-ene-2-carboxylate-5-oxide Following the same procedure as described in Example 1, Step C, m-methoxycarbonylbenzyl 3-acetyloxymethyl-7α-methoxy-8-oxo-5-thia-1-azabicyclo[4.2.0]-oct-2-ene-2-carboxylate is oxidized to m-methoxycarbonylbenzyl 3-acetyloxymethyl-7α-methoxy-8-oxo-5-thia-1-azabicyclo[4.2.0]oct-2-ene-2-carboxylate-5-oxide.

Following substantially the same procedure as described above but substituting for the N,N'-diisopropyl-O-(m-methoxycarbonylbenzyl)-isourea used therein N,N'-diisopropyl-O-(p-(p-methoxybenzyloxy)carbonylbenzyl)-isourea, there was prepared p-(p-methoxybenzyloxy)carbonylbenzyl 3-acetyloxymethyl-7α-methoxy-8-oxo-5-thia-1-azabicyclo[4.2.0]oct-2-ene-2-carboxylate as an oil, NMR (CDCl₃) δ 2.02 (s, 3), 3.42 (ABq, 2, 19 Hz), 3.53 (s, 3), 3.73 (s, 3), 4.44 (d, 1, 2 Hz), 4.62 (d, 1, 2 Hz), 4.80 (ABq, 2, 13 Hz), 5.27 (ABq, 2, 13 Hz), 6.7–8.1 (m, 8).

Subsequently, following the usual procedure as described in Example 1, Step C, the above ester was oxidized to p-(p-methoxybenzyloxy)carbonylbenzyl 3-acetyloxymethyl-7α-methoxy-8-oxo-5-thia-1-azabicyclo[4.2.0]oct-2-ene-2-carboxylate-5-oxide.

EXAMPLE 7 p-Hydroxycarbonylbenzyl 3-acetyloxymethyl-7α-methoxy-8-oxo-5-thia-1-azabicyclo[4.2.0]oct-2-ene-2-carboxylate-5-oxide A solution of 35 mg (0.061 mmols) of m-methoxybenzyl 3-acetyloxymethyl-7α-methoxy-8-oxo-5-thia-1-azabicyclo[4.2.0]oct-2-ene-2-carboxylate-5-oxide in 0.8 ml of trifluoroacetic acid is stirred with 0.2 ml of anisole at 0° C. for 15 minutes. The reaction is concentrated in vacuo and the residue is purified on a 1000 mm silica preparative plate using 1% acetic acid in 50% ethyl acetate-hexane as solvent to afford p-hydroxycarbonyl-benzyl-3-acetyloxymethyl-7α-methoxy-8-oxo-5-thia-1-azabicyclo[4.2.0]oct-2-ene-2-carboxylate-5-oxide.

EXAMPLE 8 t-Butoxycarbonylmethyl 3-acetyloxymethyl-7α-methoxy-8-oxo-5-thia-1-azabicyclo[4.2.0]oct-2-ene-2-carboxylate-5-oxide A solution of 500 mg (1.7 mmols) 3-acetyloxymethyl-7α-methoxy-8-oxo-5-thia-1-azabicyclo[4.2.0]oct-2-ene-2-carboxylic acid in 2 ml of N,N-dimethylacetamide was stirred with 300 mg (3.4 mmols) of sodium bicarbonate and 525 mg (3.4 mmoles) of t-butyl chloroacetate at room temperature for 16 hours. The reaction was diluted with water and extracted with methylene chloride. The organic layer was washed with water and saturated aqueous sodium chloride solution dried over sodium sulfate and evaporated in vacuo. The residue was chromatographed on silica gel to give 20 mg of the t-butoxycarbonylmethyl ester as a mixture of 3-ene and 2-ene isomers which is oxidized directly, by following the procedure described in Example 1, Step C, to give t-butoxycarbonylmethyl 3-acetyl-oxymethyl-7α-methoxy-8-oxo-5-thia-1-azabicyclo[4.2.0]oct-2-ene-2-carboxylate-5-oxide.

EXAMPLE 9

N-Benzyl-N-methyl 3-acetyloxymethyl-7α-methoxy-8-oxo-5-thia-1-azabicyclo[4.2.0]oct-2-ene-2-carboxylate-5-oxide A solution of 2.0 g (7.0 mmol) of 3-acetyloxymethyl-7α-methoxy-8-oxo-5-thia-1-azabicyclo[4.2.0]-oct-2-ene-2-carboxylic acid in 10 ml of dioxane and 20 ml of acetone was stirred with 1.0 g (7.0 mmols) of isobutyl chloroformate and 600 μl (7.0 mmols) of pyridine at $-15°$ C. After 20 minutes 2.5 g (21 mmoles) of N-methylbenzylamine was added and the reaction is stirred at $-15°$ C. for 1 hour, then allowed to warm to room temperature for 2 hours. The reaction was quenched with dilute hydrochloric acid and extracted into methylene chloride. The organic layer was washed with saturated aqueous sodium bicarbonate solution and saturated aqueous sodium chloride solution, dried over sodium sulfate and evaporated. The residue was chromatographed on silica gel to give 280 mg (10%) of N-benzyl-N-methyl 3-acetyloxymethyl-7α-methoxy-8-oxo-5-thia-1-azabicyclo[4.2.0]oct-2-ene-2-carboxylate, NMR (CDClR$_3$) δ 1.97 and 2.00 (s, 3), 2.83 and 2.90 (s, 3), 3.0 to 3.7 (m, 5), 4.3 to 4.8 (m, 6), 7.3 (br s, 5).

Following similar procedures as described in Example 1, Step C, N-benzyl-N-methyl 3-acetyloxymethyl-7α-methoxy-8-oxo-5-thia-1-azabicyclo[4.2.0]oct-2-ene-2-carboxylate is oxidized to give N-benzyl-N-methyl 3-acetyloxymethyl-7α-methoxy-8-oxo-5-thia-1-azabicyclo[4.2.0]oct-2-ene-2-carboxylate-5-oxide.

EXAMPLE 10

N-(t-Butoxycarbonyl)methyl 3-acetyloxymethyl-7α-methoxy-8-oxo-5-thia-1-azabicyclo[4.2.0]oct-2-ene-2-carboxamide-5-oxide A solution of 1.0 g (3.4 mmoles) of 3-acetyloxymethyl-7α-methoxy-8-oxo-5-thia-1-azabicyclo[4.2.0]-oct-2-ene-2-carboxylic acid in 25 ml of methylene chloride was stirred with 1.1 g (5.1 mmole) of dicyclohexylcarbodiimide and 450 mg (3.4 mmols) of tert-butyl glycinate at room temperature for 4 hours. The reaction was concentrated in vacuo and the residue was eluted through a short column of silica gel using 50–60% ethyl acetate-hexane. The fractions containing the resulting amide were combined and evaporated. The residue was further purified by chromatography on silica gel to give 230 mg (17%) of N-(t-butoxycarbonyl)methyl 3-acetyloxymethyl-7α-methoxy-8-oxo-5-thia-1-azabicyclo[4.2.0]oct-2-ene-2-carboxamide NMR (CDCl$_3$) δ 1.46 (s, 9), 2.07 (s, 3), 3.1–3.6 (m, 2), 3.50 (s, 3), 3.8–4.1 (m, 2), 4.47 (br s, 1), 4.63 (br s, 1), 4.87 (ABq, 2, 13 Hz), 7.4 (br s, 1).

Following similar procedures as described in Example 1, Step C, N-(t-butoxycarbonyl)methyl 3-acetyloxymethyl-7α-methoxy-8-oxo-5-thia-1-azabicyclo[4.2.-0]oct-2-ene-2-formamide is oxidized to N-(t-butoxycarbonyl)methyl 3-acetyloxymethyl-7α-methoxy-8-oxo-5-thia-1-azabicyclo[4.2.0]oct-2-ene-2-formamide-5-oxide.

EXAMPLE 11

Benzyl 3-acetyloxymethyl-7α-methoxy-8-oxo-5-thia-1-azabicyclo[4.2.0]oct-2-ene-2-carboxylate-5-oxide Step A: Preparation of Benzyl 3-acetyloxymethyl-7α-methoxy-8-oxo-5-thia-1-azabicyclo[4.2.0]oct-2-ene-2-carboxylate Trifluoroacetic acid (5 ml) was added to 316 mg (0.92 mm) of t-butyl 3-acetyloxymethyl-7α-methoxy-8-oxo-5-thia-1-azabicyclo[4.2.0]oct-2-ene-2-carboxylate with cooling in an ice bath. After stirring for 0.5 hr at 0° C., trifluoroacetic acid was evaporated in vacuo. The residue was diluted with dichloromethane and washed with cold water and brine. The dichloromethane solution was dried over sodium sulfate. Crude 3-acetyloxymethyl-7α-methoxy-8-oxo-5-thia-1-azabicyclo[4.2.0]oct-2-ene-2-carboxylic acid was obtained upon concentration of the filtrate. It was dissolved in 5 ml of tetrahydrofuran and N,N'-diisopropyl-O-benzyl-isourea (0.33 ml, 2.5 mmol) was added. After stirring for 80 hours the reaction mixture was poured into 7% sodium bicarbonate solution and extracted with ethyl acetate. The combined organic extract was washed with brine and dried over sodium sulfate. The concentrated filtrate was flash chromatographed using 50% ethyl acetatehexane to yield 259 mg (77% yield) of benzyl 3-acetyloxymethyl-7α-methoxy-8-oxo-5-thia-1-azabicyclo[4.2.0]-oct-2-ene-2-carboxylate as a mixture of 3-ene and 2-ene isomers. NMR(CDCl$_3$): δ 1.96 and 1.98 (s, 3), 3.4 (ABq, 0.8, 17 Hz), 3.43 (s, 1.8), 3.47 (s, 1.2), 4.2–5.3 (m, 6.6), 6.34 (bs, 0.6), 7–7.4 (m, 5).

Step B: Preparation of Benzyl 3-acetyloxymethyl-7α-methoxy-8-oxo-5-thia-1-azabicyclo[4.2.0]-oct-2-ene-2-carboxylate-5-oxide A solution of 145 mg (0.38 mmol) of benzyl 3-acetyloxymethyl-7α-methoxy-8-oxo-5-thia-1-azabicyclo[4.2.0]oct-2-ene-2-carboxylate in 5 ml of dichloromethane was cooled in a −78° C. bath. A solution of 75 mg (85%, 0.38 mmol) of m-chloroperbenzoic acid in 2 ml of dichloromethane is added. After 25 minutes, the cold bath was removed and the solution was allowed to warm to room temperature during the next 0.5 hour. The reaction mixture was poured into 7% sodium bicarbonate solution containing excess sodium sulfite and extracted with dichloromethane. The combined dichloromethane extract was washed with brine and dried over sodium sulfate. Concentration of the filtrate furnished benzyl 3-acetyloxymethyl-7α-methoxy-8-oxo-5-thia-1-azabicyclo[4.2.0]oct-2-ene-2-carboxylate-5-oxide as a mixture of sulfoxide isomers. $^1$HNMR (CDCl$_3$): δ 2 (s, 3), 3.22 (d, 1, 18 Hz), 3.54 (s, 3), 3.69 (d, 1, 18 Hz), 4.36 (bs, 1), 4.56 (d, 1, 13 Hz), 4.93 (bs, 1), 5.06 (d, 1, 13 Hz), 5.17 (m, 2), 7.1–7.6 (m, 5).

What is claimed is:

1. A pharmaceutical composition for treating elastase-mediated conditions in a mammalian species comprising a non-toxic pharmaceutical carrier and an effective amount of a compound of structural formula:

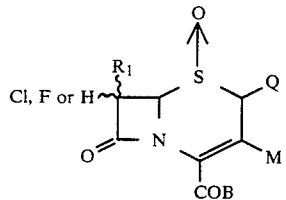

wherein M is:
   (1) hydrogen;
   (2) trifluoromethyl;
   (3) chloro or fluoro;
   (4) —COOH;
   (5) —CHO;
   (6) —CH$_2$A wherein A represents
       (a) hydrogen;
       (b) halo;
       (c) hydroxy;
       (d) alkoxy;
       (e) phenyloxy;
       (f) phenylalkoxy;
       (g) unsubstituted or substituted mercapto of formula ZR$_5$ wherein R$_5$ is H, C$_{1-6}$alkyl, phenyl, benzyl, or alkenyl;
       (h) —SCOR$_5$, or —SCOOR or SC(S)OR$_5$, —SOR$_5$ or —SO$_2$R$_5$ wherein R$_5$ is as previously defined; and R is C$_{1-6}$alkyl;
       (i) alkanoyloxy or phenylcarbonyloxy;
       (j) a substituted or unsubstituted amino or amido group selected from a group consisting of —NH$_2$, —CONH$_2$, —NHR, —N(R)$_2$, —CONHR, and —CON(R)$_2$, wherein R is C$_{1-6}$alkyl;
       (k) 3-(hydroxycarbonyl)propanoyloxy;
R$_1$ is
(1) hydroxy;
(2) —SH, —SOR, or —SO$_2$R wherein R is C$_{1-6}$alkyl;
(3) OR'$_1$ wherein R'$_1$ is C$_{1-6}$alkyl, C$_{2-6}$alkenyl, C$_{2-6}$alkynyl, phenyl or phenylalkyl;
(4) SR'$_1$ wherein R'$_1$ is as previously defined;
(5) cyano;
(6)

wherein X' is oxygen or sulfur; R" is H, halo, OH, SH, OR, SR, NHR, R, phenyl, phenylalkyl, phenyloxy, phenylalkoxy, phenylthio, phenylalkylthio or N(R)$_2$ where R is C$_{1-6}$alkyl or
(7) fluoro or chloro;
B is OB$_1$ or NB$_2$B$_3$ wherein B$_1$ and B$_2$ independently are:
   (a) straight or branched chain alkyl having from 1 to 20 carbon atoms;
   (b) phenyl;
   (c) cycloalkyl having from 3 to 8 carbon atoms;
   (d) alkenyl having from 2 to 20 carbon atoms;
   (e) cycloalkenyl having from 5 to 8 carbon atoms;
   (f) alkynyl having from 2 to 20 carbon atoms;
   (g) alkoxy alkyl having from 2 to 20 carbon atoms;
   (h) phenylalkyl or alkylphenyl;
   (i) loweralkenylalkyl;
   (j) loweralkanoylalkyl;
   (k) loweralkanoyloxyalkyl;
   (l) loweralkanoyl;
B$_3$ is B$_1$ or hydrogen; and
Q is
   (1) hydrogen;
   (2) C$_{1-6}$alkyl;
   (3) haloC$_{1-6}$alkyl;
   (4) hydroxy C$_{1-6}$alkyl;
   (5) substituted or unsubstituted C$_{1-6}$alkyl methylene, phenylmethylene, or phenylthiomethylene;
   (6) C$_{1-6}$alkoxy C$_{1-6}$alkyl;
   (7) benzyl;
   (8) phenylthio C$_{1-6}$alkyl, phenylsulfinyl C$_{1-6}$alkyl or phenylsulfonyl C$_{1-6}$alkyl;
   (9) phenoxy C$_{1-6}$alkyl; or
   (10) phenylamino C$_{1-6}$alkyl.

2. The composition of claim 1 wherein:
M is
   (1) trifluoromethyl;
   (2) chloro or fluoro;
   (3) —COOH;
   (4) —CH$_2$A wherein A represents:
       (a) hydrogen;
       (b) halo;
       (c) hydroxy;
       (d) alkoxy;
       (e) phenyloxy;
       (f) phenylalkoxy;
       (g) mercapto;
       (h) SCOR, SCOOR, SCSOR; or
       (i) OCOR;
R$_1$ is
   (1) hydroxy;
   (2) OR$_1$ where R$_1$' is as previously defined;
   (3) C$_{1-6}$alkylthio;
   (4) C$_{1-6}$alkylsulfinyl;
   (5) C$_{1-6}$alkylsulfonyl;
   (6) fluoro or chloro;
B is OB$_1$ or NB$_2$B$_3$ wherein B$_1$ and B$_2$ independently are
   (1) phenylalkyl;
   (2) phenyl;
   (3) straight or branched loweralkyl;
   (4) straight or branched loweralkenyl;
   (5) cycloalkyl;
   (6) alkanoyloxyloweralkyl;

(7) alkanoylloweralkyl;
(8) alkoxyloweralkyl; or
(9) haloalkyl; and

B₃ is hydrogen or B₁; and

Q is
(1) hydrogen;
(2) C₁₋₆alkyl;
(3) C₁₋₆alkyl methylene or phenylmethylene;
(4) phenylthio C₁₋₆alkyl.

3. The composition of claim 1 wherein:

M is
(1) trifluoromethyl;
(2) chloro or fluoro; or
(3) —CH₂A wherein A represents
   (a) alkanoyloxy;
   (b) alkoxy;
   (c) halo;
   (d) hydrogen;
   (e) hydroxy;
   (f) substituted or unsubstituted mercapto of formula SR₅ wherein R₅ is as previously defined; or
   (g) carbamoyloxy of formula L: or

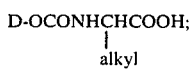

R₁ is
(1) C₁₋₆alkyl;
(1) hydroxy;
(2) OR₁' where R₁' is
   (a) C₁₋₆alkyl;
   (c) —CH₂CH₂C₆H₅; or
   (d)

where R represents hydrogen, C₁₋₆alkyl, phenyl, benzyl, or C₁₋₆alkylamino; or
(3) fluoro or chloro;

B is OB₁ or NB₂B₃ wherein B₁ and B₂ independently represent
(1) benzyl;
(2) ethyl;
(3) t-butyl;
(4) —CH₂CH₂CH=CH₂ or —CH₂CH=C(CH₃)₂;
(5) —CH₂CH₂CH₂COOt-Bu;
(6) alkanoyloxymethyl; or
(7) alkanoylmethyl;

B₃ is hydrogen or B₁; and

Q is
(1) hydrogen;
(2) methyl, ethyl or i- or n-propyl;
(3) methylene; or
(4) phenylthiomethyl or phenyl sulfonylmethyl.

4. A method of treating or management of elastase mediated conditions comprising the administration to a mammalian species in need of such treatment an effective amount of a compound of structural formula:

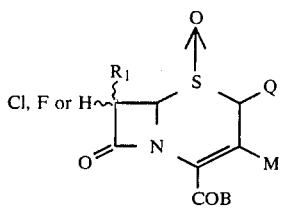

wherein M is:
(1) hydrogen;
(2) trifluoromethyl;
(3) chloro or fluoro;
(4) —COOH;
(5) —CHO;
(6) —CH₂A wherein A represents
   (a) hydrogen;
   (b) halo;
   (c) hydroxy;
   (d) alkoxy;
   (e) phenyloxy;
   (f) phenylalkoxy;
   (g) unsubstituted or substituted mercapto of formula ZR₅ wherein R₅ is H, C₁₋₆alkyl, phenyl, benzyl, or alkenyl;
   (h) —SCOR₅, or —SCOOR or SC(S)OR₅, —SOR₅ or —SO₂R₅ wherein R₅ is as previously defined; and R is C₁₋₆alkyl;
   (i) alkanoyloxy, phenylcarbonyloxy;
   (j) a substituted or unsubstituted amino or amido group selected from a group consisting of —NH₂, —CONH₂, —NHR, —N(R)₂, —CONHR, and —CON(R)₂, wherein R is C₁₋₆alkyl;
   (k) 3-(hydroxycarbonyl)propanoyloxy;

R₁ is
(1) hydroxy;
(2) —SH, —SOR, or —SO₂R wherein R is C₁₋₆alkyl;
(3) OR'₁ wherein R'₁ is C₁₋₆alkyl, C₂₋₆alkenyl, C₂₋₆alkynyl, phenyl or phenylalkyl;
(4) SR'₁ wherein R'₁ is as previously defined;
(5) cyano;
(6)

wherein X' is oxygen or sulfur; R" is H, halo, OH, SH, OR, SR, NHR, R, phenyl, phenylalkyl, phenyloxy, phenylalkoxy, phenylthio or N(R)₂ where R is C₁₋₆alkyl; or
(7) fluoro or chloro;

B is OB₁ or NB₂B₃ wherein B₁ and B₂ independently are:
(a) straight or branched chain alkyl having from 1 to 20 carbon atoms;
(b) phenyl;
(c) cycloalkyl having from 3 to 8 carbon atoms;
(d) alkenyl having from 2 to 20 carbon atoms;
(e) cycloalkenyl having from 5 to 8 carbon atoms;
(f) alkynyl having from 2 to 20 carbon atoms;
(g) alkoxy alkyl having from 2 to 20 carbon atoms;
(h) phenylalkyl or alkylphenyl;
(i) loweralkenylalkyl;
(j) loweralkanoylalkyl;
(k) loweralkanoyloxyalkyl;
(l) loweralkanoyl;

B₃ is B₁ or hydrogen; and
Q is
  (1) hydrogen;
  (2) $C_{1-6}$alkyl;
  (3) halo$C_{1-6}$alkyl;
  (4) hydroxy $C_{1-6}$alkyl;
  (5) substituted or unsubstituted $C_{1-6}$alkyl methylene, phenylmethylene, or phenylthiomethylene;
  (6) $C_{1-6}$alkoxy $C_{1-6}$alkyl;
  (7) benzyl;
  (8) phenylthio $C_{1-6}$alkyl, phenylsulfinyl $C_{1-6}$alkyl or phenylsulfonyl $C_{1-6}$alkyl;
  (9) phenoxy $C_{1-6}$alkyl; or
  (10) phenylamino $C_{1-6}$alkyl.

5. The method of claim 4 wherein:
M is
  (1) trifluoromethyl;
  (2) chloro or fluoro;
  (3) —COOH;
  (4) —CH₂A wherein A represents:
    (a) hydrogen;
    (b) halo;
    (c) hydroxy;
    (d) alkoxy;
    (e) phenyloxy;
    (f) phenylalkoxy;
    (g) mercapto;
    (h) SCOR, SCOOR, SCSOR; or
    (i) OCOR;
$R_1$ is
  (1) hydroxy;
  (2) $OR_1'$ where $R_1'$ is as previously defined;
  (3) $C_{1-6}$akylthio;
  (4) $C_{1-6}$alkylsulfinyl;
  (5) $C_{1-6}$alkylsulfonyl;
  (6) fluoro or chloro;
B is $OB_1$ or $NB_2B_3$ wherein $B_1$ and $B_2$ independently are
  (1) phenylalkyl;
  (2) phenyl;
  (3) straight or branched loweralkyl;
  (4) straight or branched loweralkenyl;
  (5) cycloalkyl;
  (6) alkanoyloxyloweralkyl;
  (7) alkanoylloweralkyl;
  (8) alkoxyloweralkyl; or
  (9) haloalkyl; and
B₃ is hydrogen or B₁; and
Q is
  (1) hydrogen;
  (2) $C_{1-6}$alkyl;
  (3) $C_{1-6}$alkyl methylene or phenylmethylene;
  (4) phenylthio $C_{1-6}$alkyl.

6. The method of claim 4 wherein:
M is
  (1) trifluoromethyl;
  (2) chloro or fluoro; or
  (3) —CH₂A wherein A represents
    (a) alkanoyloxy;
    (b) alkoxy;
    (c) halo;
    (d) hydrogen;
    (e) hydroxy;
    (f) substituted or unsubstituted mercapto of formula SR₅ wherein R₅ is as previously defined; or
    (g) carbamoyloxy of formula L- or D-OCONHCHCOOH;
         |
        alkyl $R_1$ is
  (1) $C_{1-6}$alkyl;
  (1) hydroxy;
  (2) $OR_1'$ wherein $R_1'$ is
    (a) $C_{1-6}$alkyl;
    (b) —C₆H₅;
    (c) —CH₂CH₂C₆H₅; or
    (d)

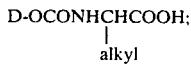

where R represents hydrogen, $C_{1-6}$alkyl, phenyl, benzyl, or $C_{1-6}$alkylamino; or
  (3) fluoro or chloro;
B is $OB_1$ or $NB_2B_3$ wherein $B_1$ and $B_2$ independently represent
  (1) benzyl;
  (2) ethyl;
  (3) t-butyl;
  (4) —CH₂CH₂CH=CH₂ or —CH₂CH=C(CH₃)₂;
  (5) —CH₂CH₂CH₂COOt-Bu;
  (6) alkanoyloxymethyl; or
  (7) alkanoylmethyl;
B₃ is hydrogen or B₁; and
Q is
  (1) hydrogen;
  (2) methyl, ethyl or i- or n-propyl;
  (3) methylene; or
  (4) phenylthiomethyl or phenyl sulfonylmethyl.

7. The composition of claim 1 wherein the active compound is
  (a) t-Butyl 3-acetyloxymethyl-7α-methoxy-8-oxo-5-thia-1-azabicyclo[4.2.0]oct-2-ene-2-carboxylate-5-oxide;
  (b) t-Butyl 3-Hydroxycarboxylethylcarbonyloxymethyl-7α-methoxy-8-oxo-5-thia-1-azabicyclo[4.2.0]oct-2-ene-2-carboxylate-5-oxide;
  (c) t-Butyl 3-chloromethyl-7α-methoxy-8-oxo-5-thia-1-azabicyclo[4.2.0]oct-2-ene-2-carboxylate-5-oxide;
  (d) m-Methoxycarbonylbenzyl-3-acetyloxymethyl-7α-methoxy-8-oxo-5-thia-1-azabicyclo[4.2.0]oct-2-ene-2-carboxylate-5-oxide;
  (e) p-Hydroxycarbonylbenzyl 3-acetyloxymethyl-7α-methoxy-8-oxo-5-thia-1-azabicyclo[4.2.0]oct-2-ene-2-carboxylate-5-oxide;
  (f) t-Butoxycarbonylmethyl 3-acetyloxymethyl-7α-methoxy-8-oxo-5-thia-1-azabicyclo[4.2.0]oct-2-ene-2-carboxylate-5-oxide;
  (g) N-benzyl-N-methyl 3-acetyloxymethyl-7α-methoxy-8-oxo-5-thia-1-azabicyclo[4.2.0]oct-2-ene-2-carboxylate-5-oxide;
  (h) N-(t-butoxycarbonyl)methyl 3-acetyloxymethyl-7α-methoxy-8-oxo-5-thia-1-azabicyclo[4.2.0]oct-2-ene-2-carboxamide-5-oxide;
  (i) Benzyl 3-acetyloxymethyl-7α-methoxy-8-oxo-5-thia-1-azabicyclo[4.2.0]oct-2-ene-2-carboxylate-5-oxide; or
  (j) Methyl-3-acetyloxymethyl-7α-methoxy-8-oxo-5-thia-1-azabicyclo[4.2.0]oct-2-ene-2-carboxylate-5-oxide.

8. The composition of claim 1 wherein the active compound is
 (a) t-Butyl 3-acetyloxymethyl-7,7-dichloro-8-oxo-5-thia-1-azabicyclo[4.2.0]oct-2-ene-2-carboxylate-5-oxide;
 (b) t-Butyl 3-acetyloxymethyl-7α-fluoro-8-oxo-5-thia-1-azabicyclo[4.2.0]oct-2-ene-2-carboxylate-5-oxide; or
 (c) t-Butyl 3-acetyloxymethyl-7α-chloro-8-oxo-5-thia-1-azabicyclo[4.2.0]oct-2-ene-2-carboxylate-5-oxide.

9. The method of claim 4 wherein the active compound
 (a) t-Butyl 3-acetyloxymethyl-7α-methoxy-8-oxo-5-thia-1-azabicyclo[4.2.0]oct-2-ene-2-carboxylate-5-oxide;
 (b) t-Butyl 3-Hydroxycarboxylethylcarbonyloxymethyl-7α-methoxy-8-oxo-5-thia-1-azabicyclo[4.2.0]oct-2-ene-2-carboxylate-5-oxide;
 (c) t-Butyl 3-chloromethyl-7α-methoxy-8-oxo-5-thia-1-azabicyclo[4.2.0]oct-2-ene-2-carboxylate-5-oxide;
 (d) m-Methoxycarbonylbenzyl-3-acetyloxymethyl-7α-methoxy-8-oxo-5-thia-1-azabicyclo[4.2.0]oct-2-ene-2-carboxylate-5-oxide;
 (e) p-Hydroxycarbonylbenzyl 3-acetyloxymethyl-7α-methoxy-8-oxo-5-thia-1-azabicyclo[4.2.0]oct-2-ene-2-carboxylate-5-oxide;
 (f) t-Butoxycarbonylmethyl 3-acetyloxymethyl-7α-methoxy-8-oxo-5-thia-1-azabicyclo[4.2.0]oct-2-ene-2-carboxylate-5-oxide;
 (g) N-benzyl-N-methyl 3-acetyloxymethyl-7α-methoxy-8-oxo-5-thia-1-azabicyclo[4.2.0]oct-2-ene-2-carboxylate-5-oxide;
 (h) N-(t-butoxycarbonyl)methyl 3-acetyloxymethyl-7α-methoxy-8-oxo-5-thia-1-azabicyclo[4.2.0]oct-2-ene-2-carboxamide-5-oxide;
 (i) Benzyl 3-acetyloxymethyl-7α-methoxy-8-oxo-5-thia-1-azabicyclo[4.2.0]oct-2-ene-2-carboxylate-5-oxide; or
 (j) Methyl 3-acetyloxymethyl-7α-methoxy-8-oxo-5-thia-1-azabicyclo[4.2.0]oct-2-ene-2-carboxylate-5-oxide.

10. The method of claim 4 wherein the active compound is
 (a) t-Butyl 3-acetyloxymethyl-7,7-dichloro-8-oxo-5-thia-1-azabicyclo[4.2.0]oct-2-ene-2-carboxylate-5-oxide;
 (b) t-Butyl 3-acetyloxymethyl-7α-fluoro-8-oxo-5-thia-1-azabicyclo[4.2.0]oct-2-and--carboxylate-5-oxide; or
 (c) t-Butyl 3-acetyloxymethyl-7α-chloro-8-oxo-5-thia-1-azabicyclo[4.2.0]oct-2-ene-2-carboxylate-5-oxide.

* * * * *